United States Patent [19]

Okumura et al.

[11] 4,077,911

[45] Mar. 7, 1978

[54] LIQUID DETERGENT OF REDUCED COLOR FADING

[75] Inventors: Takeo Okumura, Sakurashi; Shizuo Hayashi, Sugitomachi; Kanji Majima; Kensuke Takei, both of Wakayama, all of Japan

[73] Assignee: Kao Soap Co., Ltd., Tokyo, Japan

[21] Appl. No.: 583,789

[22] Filed: Jun. 4, 1975

[30] Foreign Application Priority Data

Jun. 7, 1974 Japan .................................. 49-64629

[51] Int. Cl.$^2$ .............................................. C11D 1/12
[52] U.S. Cl. .................. 252/550; 252/89 R; 252/DIG. 14; 252/403; 252/404; 252/407; 252/549; 252/551; 252/558; 8/74; 8/165
[58] Field of Search ................ 252/89, DIG. 14, 380, 252/381, 384, 403, 404, 407, 549, 550, 551, 558, 552–557, 559, 530–540, 397, 399; 8/74, 165

[56] References Cited

U.S. PATENT DOCUMENTS

| 2,664,383 | 12/1953 | Fox .......................................... 8/74 |
| 3,240,712 | 3/1966 | Schulerud ...................... 252/554 X |
| 3,716,328 | 2/1973 | Mayer ..................................... 8/165 |
| 3,755,201 | 8/1973 | Trimmer et al. ................. 252/558 X |
| 3,849,162 | 11/1974 | Mueller et al. ............................ 8/74 |
| 3,931,034 | 1/1976 | Inamorato et al. .............. 252/550 X |
| 3,972,998 | 8/1976 | Keiwer ............................. 252/549 X |

FOREIGN PATENT DOCUMENTS

| 540,214 | 4/1957 | Canada .................................. 252/550 |
| 1,231,835 | 5/1971 | United Kingdom ................. 252/550 |

OTHER PUBLICATIONS

Cosmetics Science – Technology, vol. 3, 1974, 2nd Ed. pp. 453–457.
Color Index, vol. 1, 1956, p. 1265.
The Chemistry of Synthetic Dyes–Venkataramin, vol. 1, 1952; pp. 24, 36, 39, 40, 43, 46, 47, 49, 50, 240, 244 & 245.
Printing Inks–Ellis, 1940, p. 282.

*Primary Examiner*—Mayer Weinblatt
*Attorney, Agent, or Firm*—Blanchard, Flynn, Thiel, Boutell & Tanis

[57] ABSTRACT

A colored detergent composition comprising a sulfate- or sulfonate-type anionic organic surfactant, a coloring agent, and from 0.02 to 1 percent by weight, based on the weight of said surfactant, of butylated hydroxytoluene or butylated hydroxyanisole. The detergent composition possesses the property of reduced color fading.

4 Claims, No Drawings

LIQUID DETERGENT OF REDUCED COLOR FADING

BACKGROUND OF THE INVENTION

1. Field of the Invention

This invention relates to a liquid detergent which possesses the property of substantially no color fading or reduced color fading, and which comprises as the principal effective ingredient an anionic sulfate- or sulfonate-type organic surfactant.

2. Description of the Prior Art

Anionic synthetic non-soap surfactants having a sulfate or sulfonate group are most frequently and most generally used as effective detersive ingredients of liquid detergents, such as dish washing detergents, shampoos, heavy duty liquid detergents, household detergents and the like, and they are employed in various forms.

In order to increase their commercial value, these liquid detergents are colored with various colorants. In the case of liquid detergents comprising an anionic sulfate- or sulfonate-type organic surfactant, however, there occurs extreme color fading of the detergent composition when it is exposed to sunlight for a long time or it is stored at relatively high temperatures for a long time. It is highly desirable to prevent color fading in these liquid detergents. Further, perfumes are generally incorporated in these liquid detergents, and when the detergents are stored for a long time (especially at high temperatures or in summer), these perfumes deteriorate or their fragrances change.

As a result of our research on color fading of dyes in solutions containing anionic organic surfactants containing a sulfate or a sulfonate group in the molecule, we found that minute amounts of by-products are formed during the sulfation or sulfonation reaction employed to prepare the surfactants and that the presence of these by-products in the liquid detergent composition has a great influence on color fading of the dyes or colorants therein. It was also found that if these by-products are inactivated chemically, the color fading can be considerably reduced or prevented. Based on these findings, we have now completed this invention. This is also true with respect to perfumes. Thus, by chemical inactivation of such by-products, degradation or deterioration of perfumes can be effectively reduced or prevented.

Anionic organic surfactants having a sulfate or sulfonate group in the molecule are synthesized by using highly reactive chemicals such as chlorosulfonic acid, $SO_3$ gas and propane sultone. Accordingly, in addition to the main reactions that occur, such as sulfation and sulfonation, various complicated side reactions also take place simultaneously during the synthesis process, and hence, various by-products are formed. In fact, when the characteristics of surfactants of this type are measured, peroxide values (hereinafter referred to as "POV") of a certain level are inevitably noted. Especially when $SO_3$ gas is employed as a sulfating or sulfonating agent, a high POV is observed. Accordingly, the occurrence of side reactions which produce peroxide compounds is expected in sulfation or sulfonation reactions. Although the chemical structure of the compound or compounds that provide such POV is unknown, it is found that the stability of colorants and the stability of perfumes are greatly degraded by such POV-providing compounds. More specifically, it was found that when a reducing agent, such as sodium nitrite, sodium sulfite and sodium thiosulfate, is added to an aqueous solution of an anionic surfactant of this type in an amount that precisely corresponds to the POV value thereof, the POV-providing compounds destroyed, and the stability of the colorants and perfumes is greatly improved. However, if such reducing agent is incorporated in an amount larger than the amount equimolar to the POV-providing compounds, the colorant or perfume is deteriorated and it sometimes happens that the entire solution is drastically discolored or a bad smell is generated. Accordingly, in the method in which a reducing agent is added to the detergent composition in order to prevent color fading, it is important to determine in advance the precise amount of the reducing agent that needs to be added to remove the POV-providing compounds. However, the POV differs greatly among various lots of sulfate- or sulfonate-type anionic organic surfactants, and therefore, this method requires very complex analysis procedures for measurement of the POV of each lot and determination of the amount of the reducing agent that must be added to it to remove the POV-providing compounds. Therefore, it is difficult to employ such method in practical industrial use.

SUMMARY OF THE INVENTION

We have discovered that when a specific antioxidant is added to a liquid detergent composition containing a sulfate- or sulfonate-type anionic organic surfactant, and a colorant, a very excellent effect of preventing color fading of the colorant is obtained and that even if this specific antioxidant is added in considerable excess, discoloration of the detergent composition due to deterioration or decomposition of the colorant or deterioration of the antioxidant per se is avoided.

More specifically, in accordance with this invention, there is provided a colored liquid detergent composition possessing improved color retention comprising, as indispensable ingredients, an anionic organic surfactant having a sulfate or sulfonate group in the molecule, a colorant of the coal-tar type, and 0.02 to 1.0 percent by weight, based on the weight of said anionic surfactant, of 2,6-di-tertbutyl-p-cresol (hereinafter referred to as "BHT" (butylated hydroxytoluene)) or 2-tert-butyl-4-hydroxyanisole, 3-tert-butyl-4-hydroxyanisole and mixtures thereof (hereinafter referred to as "BHA" (butylated hydroxyanisole)).

BHA and BHT are well known antioxidants, but a great number of other antioxidants are known and used in various fields. We have found that among the various known antioxidants, only BHA and BHT are not subject to discoloration by their own deterioration and can form a stable composition when blended in liquid detergents containing anionic sulfate- and sulfonate-type surfactants. BHA and BHT exhibit a very excellent effect for preventing color fading of such liquid detergent compositions. Other antioxidants either do not form stable compositions when incorporated into such detergent compositions or if they do form stable compositions, they do not exhibit an acceptable color fading-preventing effect or they readily deteriorate and discolor the detergent composition with an undesired color. Thus, it is critical to employ BHT or BHA as the antioxidant in the detergent composition according to this invention.

Further, when BHT or BHA is used, it is unnecessary to measure the POV of the detergent composition and then determine the amount of the antioxidants to be blended therein. We have found that when BHT or BHA is incorporated in the detergent composition in an amount of 0.02 to 1.0 percent by weight, based on the weight of the anionic sulfate- or sulfonate-type surfactant, an excellent effect of preventing color fading is obtained. In general, a satisfactory result is obtained when BHT or BHA is incorporated in an amount of about 100 ppm based on the entire detergent composition.

An anionic surfactant having a sulfate or sulfonate group is used as the principal active detergent substance of the liquid detergent composition. As specific examples of such water-soluble organic anionic surfactants, there can be mentioned alkylbenzenesulfonates having an alkyl group containing 8 to 16 carbon atoms on the average, alkyl sulfate having 11 to 18 carbon atoms on the average, alpha-olefinsulfonates having 10 to 20 carbon atoms on the average, alkanesulfonates having 10 to 18 carbon atoms on the average, alkylpolyoxyethylene ether sulfates having an alkyl group containing 8 to 21 carbon atoms and about 1 to 6 units of ethylene oxide per molecule, and alkylphenylpolyoxyethylene ether sulfates having an alkyl group containing 8 to 12 carbon atoms and about 1 to 10 units of ethylene oxide per molecule. In these anionic surfactants, the alkyl groups can be either linear or branched alkyl groups, or mixtures thereof. The salt-forming moieties of the surfactants can be selected from those conventionally used in water-soluble surfactants, such as sodium, potassium, ammonium, alkylolamines such as triethanolamine and diethanolamine, and magnesium. Sodium salts are preferred. The concentration of the anionic surface active agent is determined appropriately depending on the use and application object of the detergent. In general, the concentration of the anionic surface active agent is 1.0 to 30 percent by weight, preferably 5 to 20 percent by weight.

A colorant of the coal-tar type (dye) is used to color the detergent composition of this invention. The colorants (dye) of the coal-tar type are those which are approved for use in medicines, cosmetics and the like as provided by Japanese Welfare Ministry Ordinance No. 30 of 1965 and by the U.S. Code of Federal Regulations, Title 21, Subchapter A, Part 9.

The following Table sets for the Japanese Legal Color No., United States FDC Color No. and chemical name of colorants for use in this invention. In the following description the Japanese Legal Color Nos. are used, but it will be understood that these correspond to the FDC Color Nos. set forth in the Table.

| Japanese Legal Color No. | U.S. FDC Color No. | Chemical Name |
|---|---|---|
| Red No. 2 | D&C Red No. 2) FD&C Red No. Trisodium | Trisodium salt of 1-(4-sulfo-1-naphthl-azo)-2-naphthol-3,6-disulfonic acid |
| Red No. 3 | D&C Red No. 3) FD&C Red No. 3 | Disodium salt of 9-o-carboxyphenyl-6-hydroxy 2,4,5,7-tetraido 3-isoxanthene |
| Red No. 102 | — | Trisodium salt of 1-(4-sulfo-1-naphthl-azo)-2-naphthol-6,8-disulfonic acid |
| Red No. 104 | D&C Red No. 28 | Disodium salt of 2,4,5,7-tetrabromo-9-(3,4,5,6-tetrachloro-o-carboxyphenyl)-6-hydroxy-3-ixoxanthone |
| Red No. 105 | Ext. D&C Red NO. 5 | Disodium salt of 9-(3,6-dichloro-o-carboxyphcuyl)-6-hydroxy-2,4,5,7-tetraido-3-isoxanthone |
| Red No. 106 | — | Monosodium salt of 9-(4-sulfo-2-sulfoniumphenyl)-6-diethylamino-3-(N-N-diethylimino-3-isoxanthene |
| Yellow No. 4 | D&C Yellow No. 5) FD&C Yellow No. 5 | Trisodium salt 3-carboxy-5-hydroxy-1-p-sulfophenyl-1-sulfophenylazopyrazole |
| Yellow No. 5 | D&C Yellow No. 6) FD&C Yellow No. 6 | Disodium salt of 1-p-sulfophenylazo-2-naphthol-6-sulfonic acid |
| Green No. 3 | FD&C Green No. 3 | Disodium salt of 4-{[4-(N-ethyl-p-sulfobenzylamino)phenyl]-(4 hydroxy-2-sulfoniumphenyl)methylene}-[1-(N-ethyl-N-p-sulfobenzyl)-Δ2.5-cyclohexadieneimine] |
| Blue No. 1 | D&C Blue No. 1) FD&C Blue No. 1 | Disodium salt of 4-{[4-(N-ethyl-p-sulfobenzylamino)phenyl]-(2-sulfoniumphenyl) Methylene}-[1-(N-ethyl-N-p-sulfobenzyl)-Δ2.5-cyclohexadienimine] |
| Blue No. 2 | D&C Blue No. 2) FD&C Blue No. 2 | Disodium salt of 5,5-indigotindisulfonic acid |
| Green No. 202 | D&C Green No. 6 | 1,4-Bis(p-toluino)-anthraquinone |
| Green No. 204 | D&C Green No. 8 | Trisodium salt of 10-hydroxy-3,5,8-pyrenetrisulfonic acid |
| Green No. 205 | FD&C Green No. 2 | Disodium salt of 4-{[4-(N-ethyl-p-sulfobenzylamino)-phenyl](4-sulfoniumphenyl)methylene}-[1-(N-ethyl-N-p-sulfobenzyl)-Δ2.5-cyclohexadienimine-Δ |
| Blue No. 201 | D&C Blue No. 6 | Indigotin |
| Blue No. 202 | D&C Blue NO. 7 | Monosodium salt of 4-{8 4-N-ethylbenzylamino)phenyl]-5-hydroxy-4-sulfo-2-sulfoniumphenyl)-methylene}-(N-ethyl-N-benzyl-Δ2.5-cyclohexadienimine Δ |
| Blue No. 203 | D&C Blue No. 8 | Ca salt corresponding to D&C Blue No. 7 |
| Blue No. 204 | D&C Blue No. 9 | 3,3-Dichloroindanthrene |
| Blue No. 205 | D&C Blue No. 4 | NH$_4$ salt corresponding to FD&C Blue No. 1 Δ |
| Brown No. 201 | D&C Brown No. 1 | Monosodium salt of 4-p-sulfophenylazo-2-(2,4-xylylazo)-1,3-resorcinol |
| Violet No. 201 | D&C Violet No. 2 | 1-Hydroxy-4-p-toluinoathraquinone |
| Orange No. 203 | D&C Orange No. 17 | 1-(2,4-Dinitrophenylazo)-2-naphthol |
| Orange No. 204 | 1 | 3,3-dichlol-diphenyl-4.4-bisazo(1-phenyl-3-methyl-5-pyrazolone |

-continued

| Japanese Legal Color No. | U.S. FDC Color No. | Chemical Name |
|---|---|---|
| Orange No. 205 | D&C Orange No. 4 | Monosodium salt of 1-p-sulfophenylazo-2-naphthol |
| Orange No. 206 | D&C Orange No. 10 | 4,5-Diiodo-3,6-fluorandiol |
| Orange No. 207 | D&C Orange No. 11 | Disodium salt of 9-o-carboxyphenyl-6-hydroxy-4,5-diido-3-isoxanthone |
| Yellow No. 201 | D&C Yellow No. 7 | 3,6-Fluorandiol |
| Yellow No. 202-1 | D&C Yellow No. 8 | Disodium salt of 9-o-carboxyphenyl-6-hydroxy-3-isoxanthone |
| Yellow No. 202-2 | D&C Yellow No. 9 | K salt corresponding to D&C Yellow No. 8 |
| Yellow No. 203 | D&C Yellow No. 10 | Disodium salt of disulfonic acid of D&C Yellow No. 11 |
| Yellow No. 204 | D&C Yellow No. 11 | 2-(2-Quinolyl)-1,3-indandione |
| Yellow No. 205 | — | 3,3-dichlol-diphenyl-4,4-bisazo-(aceto-actolt methylanilido) |
| Green No. 201 | D&C Green No. 5 | Disodium salt of 1,4-brs(o-sulfo-p-toluino)anthraquinone |
| Red No. 201 | D&C Red No. 6 | Disodium salt of 4(o-sulfo-p-tolylazo)-3-hydroxy-2-naphthoic acid |
| Red. No. 202 | D&C Red. No. 7 | Ca salt corresponding to D&C Red No. 6 |
| Red. No. 203 | D&C Red No. 8 | Monosodium salt of 1-(4-chloro-o-sulfo-5-tolylazo)-2-naphthol |
| Red No. 204 | D&C Red No. 9 | Ba salt corresponding to D&C Red No. 8 |
| Red No. 205 | D&C Red No. 10 | Monosodium salt of 2-(2-hydroxy-1-naphthylazo)-1-naphthalenesulfonic acid |
| Red No. 206 | D&C Red No. 11 | Ca salt corresponding to D&C Red No. 10 |
| Red No. 207 | D&C Red No. 12 | Ba salt corresponding to D&C Red No. 10 |
| Red No. 208 | D&C Red No. 13 | Sr salt corresponding to D&C Red No. 10 |
| Red No. 213 | D&C Red No. 19 | 3-Ethochloride of 9-o-carboxyphenyl-6-diethylamino-3-ethylimino-3-isoxanthene |
| Red No. 214 | D&C Red No. 20 | 3-Ethoacetate of 9-o-carboxyphenyl-6-diethylamino-3-ethylimino-3-isoxanthene |
| Red No. 215 | D&C Red No. 37 | 3-Ethostearate of 9-o-carboxyphenyl-6-diethylamino-3-ethylimino-3-isoxanthene |
| Red No. 218 | D&C Red No. 27 | 2,4,5,7-Tetrabromo-12,13,14,15,-tetrachloro-3,6-fluorandiol |
| Red No. 219 | D&C Red No. 31 | Calcium salt of 3-hydroxy-1-phenylazo-1-naphthoic acid |

As typical examples of colorants of this type, there can be mentioned Red No. 3 (FD&C Red No. 3) (Erythrosine), Red No. 213 (D&C Red No. 19) (Rhodamin B), Yellow No. 4 (D&C Yellow No. 5, FD&C Yellow No. 5) (Tartrazine), Yellow No. 201 (D&C Yellow No. 7) (Fluorescein), Blue No. 1 (D&C Blue No. 1, FD&C Blue No. 1) (Brilliant Blue) and Green No. 204 (D&C Green No. 8) (Pyranine Conc). The amount used of such colorant is not critical. It is used in an amount customarily used in detergent compositions of this type (2/10000 to 5/1000 percent by weight, based on the total weight of the detergent composition).

The optimum amount of colorant differs depending on the particular kind of colorant used. For example, when Red. No. 213 is used, the optimum amount is 2/10000 percent by weight. The optimum amounts of other colorants are as follows:

| Yellow No. 4 | 3/1000 % by weight |
|---|---|
| Blue No. 1 | 5/10000 % by weight |
| Green No. 204 | 3/1000 % by weight |

It sometimes happens that a solution of a surfactant is normally colored yellow or yellowish brown. In such case, in order to obtain a good color tone of the colored liquid detergent composition, the solution is bleached by using an oxidant such as hydrogen peroxide or sodium hypochlorite. If such a bleached solution is directly used as the detergent base, because of the formation of minute amounts of peroxides (POV-providing substances) color fading or deteriorations of the dye or colorant normally occurs when the detergent is stored for a long time. Even in such case, however, when BHT or BHA is incorporated in a liquid detergent composition containing such decolored surfactant as mentioned above, color fading and deterioration of the colorant can be greatly reduced.

In addition to the critical components of the liquid detergent composition of this invention, namely, the anionic sulfate- or sulfonate-type organic surfactant, the colorant and BHT or BHA, the detergent composition can optionally contain minor amounts of various conventional additives such as emollients, solubilizing agents, nonionic surfactants, opacifying agents, sequestering agents, etc. These are used in the conventional amounts for the conventional purposes.

This invention will now be further described in detail by reference to the following illustrative Examples and Composition Examples of the detergent compositions of this invention.

EXAMPLE 1

Sodium polyoxyethylene ($\bar{P}$ = 3) dodecyl ether sulfate was used as the anionic surfactant. A typical approved colorant, i.e. Yellow No. 4 (Tartrazine) or Blue No. 1 (Brilliant Blue FCF), was incorporated in an amount of 0.0005 percent by weight into a 10 percent aqueous solution of this anionic surface active agent. Various antioxidants and reducing agents were added, respectively to the thus-formed detergent base, and their color fading-preventing effects were examined. The results shown in Tables 1 and 2 were obtained.

More specifically, an antioxidant as listed in Table 1 was added to the above aqueous solution of the surfactant so that the concentration of the anitoxidant was 100 ppm. The resulting detergent solution was filled in a polyvinyl chloride vessel and exposed to sunlight for 10 sunny days, or the vessel was stored in a room at 50° C. for 1 month. The residual amount of the colorant, the appearance of the solution (state of discoloration) and the change of its odor were examined. The residual amount of the colorant was determined by measuring the characteristic absorption at 428 m$\mu$ in the case of Yellow No. 4 and at 635 m$\mu$ in the case of Blue No. 1. The results obtained when the solution was exposed to sunlight are shown in Table 1, and the results obtained when the solution was stored at 50° C. are shown in Table 2.

Table 1

Results Obtained on Sunlight Exposure (10 days)

| Anti-oxidant | Residual Amount (%) of Colorant | | Dis-coloration | Change of Odor |
|---|---|---|---|---|
| | Yellow No. 4 | Blue No. 1 | | |
| BHT | 99.5 | 98.0 | not observed | not observed |
| BHA | 98.5 | 99.0 | not observed | not observed |
| erythorbic acid | 27.4 | 65.0 | slight | scarcely observed |
| sodium erythorbate | 27.4 | 64.0 | slight | scarcely observed |
| tocopherol | 99.5 | 98.5 | extreme* | observed |
| n-propyl gallate | 99.0 | 98.0 | extreme* | observed |
| sodium thiosulfate | 94.0 | 93.0 | scarcely observed | scarcely observed |
| sodium nitrite | 52.0 | 94.0 | slight | scarcely observed |
| not added | 47.0 | 35.0 | slight | observed |

Table 3

Influences of Concentration

| Amount (ppm) of BHT | Residual Amount (%) of Colorant | | | | Deterioration of Perfume Aroma | |
|---|---|---|---|---|---|---|
| | Storage at 50° C. | | Sunlight Exposure | | Storage at 50° C. | Sunlight Exposure |
| | Yellow No. 4 | Blue No. 1 | Yellow No. 4 | Blue No. 1 | | |
| not added | 1.4 | 10.5 | 0.6 | 4.3 | Δ | Δ |
| 10 | 1.4 | 11.3 | 1.0 | 6.5 | Δ | Δ |
| 50 | 101.2 | 100.3 | 90.5 | 94.6 | 0 | 0 |
| 100 | 100.0 | 100.9 | 90.6 | 94.1 | 0 | 0 |
| 150 | 100.0 | 100.6 | 90.3 | 94.1 | 0 | 0 |
| 200 | 100.0 | 100.6 | 90.5 | 94.3 | 0 | 0 |
| 300 | 98.7 | 101.5 | 90.5 | 94.0 | 0 | 0 |

Degree of Deterioration of Perfume:
O not changed
Δ slightly deteriorated
X considerably deteriorated
These symbols shall have the same meanings hereinafter.

Table 2

Results Obtained on Storage at 50° C. (1 month)

| Anti-oxidant | Residual Amount (%) of Colorant | | Dis-coloration | Change of Odor |
|---|---|---|---|---|
| | Yellow No. 4 | Blue No. 1 | | |
| BHT | 98.5 | 98.0 | not observed | not observed |
| BHA | 99.0 | 97.5 | not observed | not observed |
| erythorbic acid | 45.0 | 70.0 | slight | scarcely observed |
| sodium erythorbate | 46.0 | 71.0 | sight | scarcely observed |
| tocopherol | 103.7** | 106.8** | considerable* | observed |
| n-propyl gallate | 112.0** | 109.0** | considerable* | observed |
| sodium thiosulfate | 56.5 | 90.0 | scarcely observed | scarcely observed |
| sodium nitrite | 104.4** | 107.8** | considerable | scarcely observed |
| not added | 40.5 | 39.0 | slight | observed |

Notes:
*Dark brown discoloration was caused by deterioration of the antioxidant and the like.
**Since the standard line was shifted in measuring the absorbancy, the calculated value exceeded 100 percent, but in practical use, decomposition of the colorant was caused to occur.

As is apparent from the results shown in Tables 1 and 2, BHT, BHA, tocopherol and n-propyl gallate have color fading-preventing effect on either sunlight exposure or storage at 50° C. In the case of the two latter antioxidants, however, the appearance of the solution was drastically degraded by discoloration, even though no color fading in the colorant was observed at the measurement of specific absorptions. Accordingly, these antioxidants cannot be used for attaining the object of this invention, namely, maintaining a beautiful appearance of the detergent while preventing discoloration. It is believed that in the case of these latter antioxidants, the antioxidants per se were deteriorated and the solution was discolored to dark brown.

EXAMPLE 2

Sodium lauryl sulfate was used as the anionic surfactant. BHT was added to a 10 percent aqueous solution of this surfactant with various concentration of BHT, to examine the influence of the concentration of BHT on the color fading-preventing effect. Yellow No. 4 and Blue No. 1 were used as the colorants, and the colorant concentration was 0.003 percent (Yellow No. 4) or 0.0005 percent (Blue No. 1.) The test was conducted in the same manner as in Example 1, except that the storage at 50° C. was continued for 20 days. A perfume for dishwashing detergents was used. The test results are shown in Table 3.

As is apparent from the results shown in Table 3, when the concentration was 10 ppm, no substantial effect was obtained, but at a concentration of 50 ppm or higher, a highly improved effect was obtained. Accordingly, it is considered that the minimum necessary amount of the antioxidant was between 10 ppm and 50 ppm in this case. However, even when the concentration was as high as 300 ppm, no adverse effects were imparted to either the colorant or to the perfume and the solution was not discolored at all. Even at a concentration of 1000 ppm, no particular disadvantages were brought about, but at a concentration exceeding 1000 ppm, a problem concerning the solubility of BHT occurs. Similar results were obtained also with respect to BHA.

EXAMPLE 3

A 20 percent aqueous solution (sample No. 1) of sodium polyoxyethylene ($\bar{P}$ = 3.0) lauryl ether sulfate which was not bleached, the same solution (sample No. 3) decolored with sodium hypochlorite (NaClO), a solution (sample No. 2) formed by adding 100 ppm of BHT to sample No. 1, and a solution (sample No. 4) formed by adding 100 ppm of BHT to sample No. 3, were tested in the same manner as in Example 1 to determine the degree of color fading and the degree of deterioration of the perfume. Yellow No. 4, Blue No. 1, Red No. 213 (Rhodamine B) and Green No. 204 (Pyranine Conc) were used as the colorant, and a perfume for shampoos was used as the perfume. The amount added of the colorant and the wavelength for measurement of the specific absorption were as shown below:

| | Amount Added (%) | Wavelength (mµ) |
|---|---|---|
| Yellow No. 4 | 0.003 | 426 |
| Blue No. 1 | 0.0005 | 635 |
| Red No. 213 | 0.0002 | 555 |
| Green No. 204 | 0.003 | 455 |

The results obtained are shown in Table 4.

Table 4

Storage at 50° C.

| Sample No. | Additive | Days | Red No. 213 | Blue No. 1 | Yellow No. 4 | Green No. 204 | Deterioration of Perfume |
|---|---|---|---|---|---|---|---|
| 1 | not added | 10 | 93.9 | 23.6 | 2.1 | 37.3 | O |
|   |   | 25 | 88.4 | 13.7 | 1.7 | 15.1 | Δ |
| 2 | BHT 100 ppm | 10 | 98.4 | 100.0 | 98.1 | 96.5 | O |
|   |   | 25 | 99.5 | 100.9 | 98.1 | 99.2 | O |
| 3 | NaClO 100 pmm | 10 | 92.1 | 2.5 | 2.5 | 52.4 | Δ |
|   |   | 25 | 86.6 | 2.5 | 2.5 | 22.8 | X |
| 4 | NaClO 100 ppm BHT 100 ppm | 10 | 98.6 | 99.4 | 99.4 | 94.4 | O |
|   |   | 25 | 100.8 | 99.4 | 99.4 | 102.2 | O |

Stability of Colorant and Perfume

Sunlight Exposure

| Sample No. | Sunny Days | Red No. 213 | Blue No. 1 | Yellow No. 4 | Green No. 204 | Deterioration of Perfume |
|---|---|---|---|---|---|---|
| 1 | 5 | 93.4 | 53.3 | 51.4 | 64.7 | 0 |
|   | 19 | 82.7 | 19.0 | 1.3 | 49.1 | Δ |
| 2 | 5 | 96.8 | 99.0 | 97.2 | 87.4 | O |
|   | 19 | 90.5 | 98.7 | 90.6 | 73.3 | O |
| 3 | 5 | 93.1 | 70.0 | 71.5 | 74.1 | Δ |
|   | 19 | 85.4 | 37.5 | 1.6 | 54.6 | X |
| 4 | 5 | 96.5 | 99.1 | 97.8 | 85.1 | O |
|   | 19 | 90.8 | 97.8 | 90.2 | 71.6 | O |

As is apparent from the results shown in Table 4, the stability to discoloration differs among the colorants, and Red No. 213 is most stable. Even in this relatively stable colorant, the color fading-preventing effect is observed on addition of BHT. In the case of unstable colorants such as Yellow No. 4 and Blue No. 1, a conspicuous effect can be attained by addition of BHT. Moreover, also in the case of detergent compositions bleached with sodium hypochlorite, the color of which readily fades, an excellent color fading-preventing effect can be attained by addition of BHT.

Examples of compositions of the liquid detergent of this invention will now be described.

COMPOSITION EXAMPLE 1

Low viscosity opaque dishwashing detergent:

| | | |
|---|---|---|
| Sodium linear alkylbenzene-sulfonate (active comonent) | 17 % | |
| Sodium lauryl sulfate (active component) | 7 % | |
| Ethanol | 6 % | |
| Urea | 6 % | |
| Colorant (Yellow No. 4) | 0.003 % | |
| Opacifying agent (ethylene-glycol distearate) | 0.15 % | |
| Perfume | 0.1 % | |
| 10 % Solution of BHT in ethanol | 0.2 % | |
| Water | 72.547 % | |

An aqueous solution of sodium linear alkylbenzene-sulfonate and sodium lauryl sulfate was added to water, and the solution was agitated at 60° C. for 20 minutes. Urea was added to the solution, and the mixture was cooled. When the temperature was lowered to 40° C., the ethanol solution of BHT, the colorant and the perfume were added.

COMPOSITION EXAMPLE 2

Low viscosity transparent dishwashing detergent:

| | | |
|---|---|---|
| Sodium linear alkylbenzene-sulfonate | 15 % | (active component) |
| Polyoxyethylene ($\bar{P}$ = 30) nonylphenyl ether | 10 % | |
| Isopropyl alcohol | 3 % | |
| Sodium p-toluenesulfonate | 5 % | |
| Red No. 213 | 0.0001 % | |
| Perfume | 0.1 % | |
| 10 % Solution of BHA in ethanol | 0.1 % | |
| Water | 67.6 % | |

Water was maintained at 60° C., and sodium linear alkylbenzenesulfonate, polyoxyethylene nonylphenyl ether, isopropyl alcohol and sodium p-toluenesulfonate were added thereto. The mixture was agitated for 20 minutes and cooled to 40° C. Then, the colorant, the perfume and the BHA solution were added to the mixture.

COMPOSITION EXAMPLE 3

Transparent liquid shampoo:

| | | |
|---|---|---|
| Dobanol-1213 sulfate triethanol-amine salt (triethanolamine salt of sulfuric acid ester of oxo alchol having 12 to 13 carbon atoms) | 8 % | (active component) |
| Lauryl ether sulfate triethanol-amine salt | 10 % | |
| Lauryl diethanolamide | 5 % | |
| Disodium ethylenediamine-tetraacetate | 0.1 % | |
| 10 % Solution of BHT in ethanol | 0.1 % | |
| Blue No. 1 | 0.0001 % | |
| Yellow No. 4 | 0.004 % | |
| Perfume | 0.3 % | |
| Deionized water | 77.8 % | |

Deionized water was heated and maintained at 55° C., and Dobanol-1213 sulfate, lauryl ether sulfate, lauryl diethanolamide and disodium ethylenediamine-tetraacetate were added thereto. The mixture was agitated for 20 minutes and cooled to 40° C. Then, the BHT solution, the perfume and the colorants were added to the mixture, and agitation was conducted to obtain a homogeneous composition.

COMPOSITION EXAMPLE 4

Pearlescent cream shampoo:

| | | |
|---|---|---|
| Sodium lauryl sulfate | 12 % | (active component |
| Sodium lauryl ether sulfate | 5 % | (active component |
| Coconut fatty acid diethanolamide | 7 % | |
| Ethyleneglycol distearate | 7 % | |
| 10 % Solution of BHT in ethanol | 1 % | |
| Yellow No. 4 | 0.003 % | |
| Perfume | 0.2 % | |
| Water | 74.7 % | |

Water was maintained at 70° C., and sodium lauryl sulfate and sodium lauryl ether sulfate were added thereto. Then, coconut fatty acid diethanolamide and ethyleneglycol distearate, were added, and the mixture was agitated for 30 minutes to obtain a transparent composition. Then, it was cooled to 40° C., and the BHT solution, the colorant and the perfume were added thereto. The mixture was agitated for 1 hour to obtain a pearlescent cream shampoo.

The embodiments of this invention in which an exclusive property or privilege is claimed are defined as follows:

1. A colored liquid detergent composition possessing improved color stability, consisting essentially of: from one to 30 percent by weight of anionic synthetic nonsoap surfactant having a sulfate or sulfonate group in the molecule, from 0.0002 to 0.0005 percent by weight of a colorant of the coal-tar type approved for use in cosmetic and pharmaceutical compositions, from 0.02 to 1.0 percent by weight, based on the weight of said anionic surfactant, of butylated hydroxytoluene or butylated hydroxyanisole, and the balance is water, optionally containing conventional additives for liquid detergents.

2. A colored liquid detergent as claimed in claim 1, in which said anionic surfactant is selected from the group consisting of alkylbenzenesulfonates having an alkyl group containing 8 to 16 carbon atoms on the average, monoalkyl sulfuric acid ester salts having 11 to 18 carbon atoms on the average, alpha-olefinsulfonates having 10 to 20 carbon atoms on the average, alkanesulfonates having 10 to 18 carbon atoms on the average, alkyl-polyoxyethylene ether sulfuric acid ester salts having an alkyl group containing 8 to 21 carbon atoms and about 1 to 6 ethylene oxide units in the molecule and alkylphenyl-polyoxyethylene ether sulfuric acid ester salts having an alkyl group containing 8 to 12 carbon atoms and about 1 to 10 ethylene oxide units in the molecule, said alkyl groups being either linear or branched chain, and mixtures thereof.

3. A colored liquid detergent composition as claimed in claim 1 containing 5 to 20 percent by weight of said anionic surfactant and about 100 ppm of butylated hydroxytoluene or butylated hydroxyanisole.

4. A colored liquid detergent composition as claimed in claim 1 in which the amount of butylated hydroxytoluene or butylated hydroxy anisole is from 50 to 1000 ppm.

* * * * *

UNITED STATES PATENT AND TRADEMARK OFFICE
CERTIFICATE OF CORRECTION

PATENT NO. : 4 077 911
DATED : March 7, 1978
INVENTOR(S) : Takeo Okumura et al

It is certified that error appears in the above-identified patent and that said Letters Patent are hereby corrected as shown below:

Column 11, line 27; change "0.0005" to ---0.005---.

Signed and Sealed this

Fourth Day of July 1978

[SEAL]

Attest:

RUTH C. MASON
*Attesting Officer*

DONALD W. BANNER
*Commissioner of Patents and Trademarks*